(12) United States Patent
Abe et al.

(10) Patent No.: US 7,393,349 B2
(45) Date of Patent: Jul. 1, 2008

(54) OPHTHALMIC LASER TREATMENT APPARATUS

(75) Inventors: Hitoshi Abe, Okazaki (JP); Seiki Tomita, Gamagori (JP); Masato Kawai, Gamagori (JP)

(73) Assignee: Nidek Co., Ltd., Gamagori (JP)

( * ) Notice: Subject to any disclaimer, the term of this patent is extended or adjusted under 35 U.S.C. 154(b) by 59 days.

(21) Appl. No.: 11/390,106

(22) Filed: Mar. 28, 2006

(65) Prior Publication Data
US 2006/0224147 A1    Oct. 5, 2006

(30) Foreign Application Priority Data
Mar. 31, 2005    (JP) .............................. 2005-105378

(51) Int. Cl.
*A61B 18/18* (2006.01)
*G06F 3/01* (2006.01)

(52) U.S. Cl. ................................ 606/4; 606/10; 606/12; 708/139

(58) Field of Classification Search .................... 606/4, 606/5, 10–12; 273/148; 708/139; 341/20, 341/21, 23–26, 29, 30, 35
See application file for complete search history.

(56) References Cited

U.S. PATENT DOCUMENTS

| | | | | |
|---|---|---|---|---|
| 5,098,426 A | * | 3/1992 | Sklar et al. | 606/5 |
| 6,235,014 B1 | * | 5/2001 | Abe et al. | 606/4 |
| 6,245,058 B1 | * | 6/2001 | Suzuki | 606/2 |
| 6,383,178 B1 | * | 5/2002 | Abe | 606/11 |
| 6,585,723 B1 | * | 7/2003 | Sumiya | 606/5 |
| 6,669,684 B2 | * | 12/2003 | Nakamura | 606/5 |
| 6,673,061 B2 | * | 1/2004 | Abe | 606/4 |
| 6,712,808 B2 | * | 3/2004 | Fujieda | 606/4 |
| 6,932,807 B1 | * | 8/2005 | Tomita et al. | 606/10 |
| 7,033,346 B2 | * | 4/2006 | Previn et al. | 606/4 |
| 7,229,435 B2 | * | 6/2007 | Nakamura | 606/4 |

FOREIGN PATENT DOCUMENTS

JP    A-2000-217839    8/2000
JP    A-2001-161739    6/2001

\* cited by examiner

*Primary Examiner*—Ahmed M Farah
(74) *Attorney, Agent, or Firm*—Oliff & Berridge, PLC

(57) ABSTRACT

An ophthalmic laser treatment apparatus comprises: a main unit in which an illumination and observation optical system for illuminating a patient's eye and allowing observation of the patient's eye under illumination, and an irradiation optical system for irradiating a treatment laser beam and an aiming beam to the patient's eye; a joystick including a grip to be grasped by an operator, the joystick being configured to move the main unit with respect to the patient's eye; and a switch placed in an opening formed in a side of the joystick, the switch being configured to input a plurality of switch signals.

7 Claims, 6 Drawing Sheets

SECTION A-A

|  | FIRST SW SIGNAL | SECOND SW SIGNAL | THIRD SW SIGNAL |
|---|---|---|---|
| PATTERN 1 | SWITCH TO READY/STANDBY MODE | INCREASE ENERGY OF TREATMENT BEAM | DECREASE ENERGY OF TREATMENT BEAM |
| PATTERN 2 | SWITCH TO BURST MODE | INCREASE LIGHT QUANTITY OF AIMING BEAM | DECREASE LIGHT QUANTITY OF AIMING BEAM |
| PATTERN 3 | ROTATE AIMING BEAM | BACKWARD FOCUS SHIFT | FORWARD FOCUS SHIFT |

OPHTHALMIC LASER TREATMENT APPARATUS

BACKGROUND OF THE INVENTION

1. Field of the Invention

The present invention relates to an ophthalmic laser treatment apparatus for treating an affected part of a patient's eye by irradiating a treatment laser beam to the affected part.

2. Description of Related Art

An ophthalmic laser treatment apparatus is arranged to perform alignment (positioning) by moving a main unit housing an illumination and observation optical system and an irradiation optical system for a treatment laser beam relative to a patient's eye. The main unit is normally moved by tilting operation of a joystick. After completion of the alignment, irradiation conditions of the treatment beam are set by operation of a switch section in accordance with a treatment purpose, the current status of the patient's eye, and others.

The joystick and the switch section are provided in separate positions. In the case that the switch section is to be operated after completion of the alignment, an operator has to first take his/her hand off the joystick. At this time, the alignment may become off. It is therefore conceivable that the switch section is provided in the joystick. However, the switch section merely provided in such a manner may be erroneously operated at the time of operation of the joystick. Further, there are limits to the number of switches incorporable in a narrow area of the joystick. On the contrary, such configuration may cause difficulty in operating.

BRIEF SUMMARY OF THE INVENTION

The present invention has been made in view of the above circumstances and has an object and to provide an ophthalmic laser treatment apparatus including a joystick provided with a switch easy to operate, which causes less erroneous operation.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided an ophthalmic laser treatment apparatus comprising: a main unit in which an illumination and observation optical system for illuminating a patient's eye and allowing observation of the patient's eye under illumination, and an irradiation optical system for irradiating a treatment laser beam and an aiming beam to the patient's eye; a joystick including a grip to be grasped by an operator, the joystick being configured to move the main unit with respect to the patient's eye; and a switch placed in an opening formed in a side of the joystick, the switch being configured to input a plurality of switch signals.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
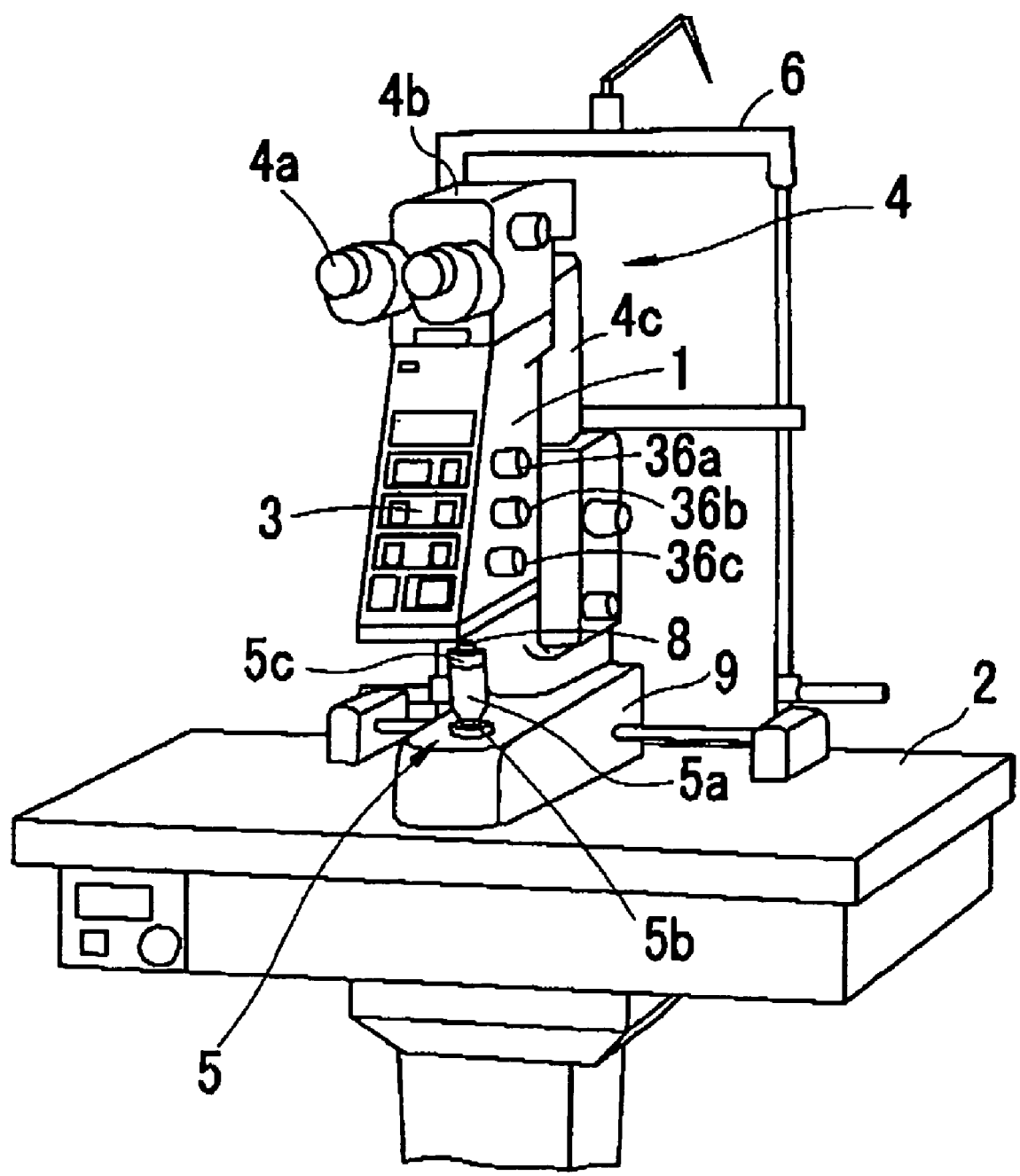
FIG. 1 is a schematic perspective view of an ophthalmic laser treatment apparatus in an embodiment of the present invention.
Figure 2:
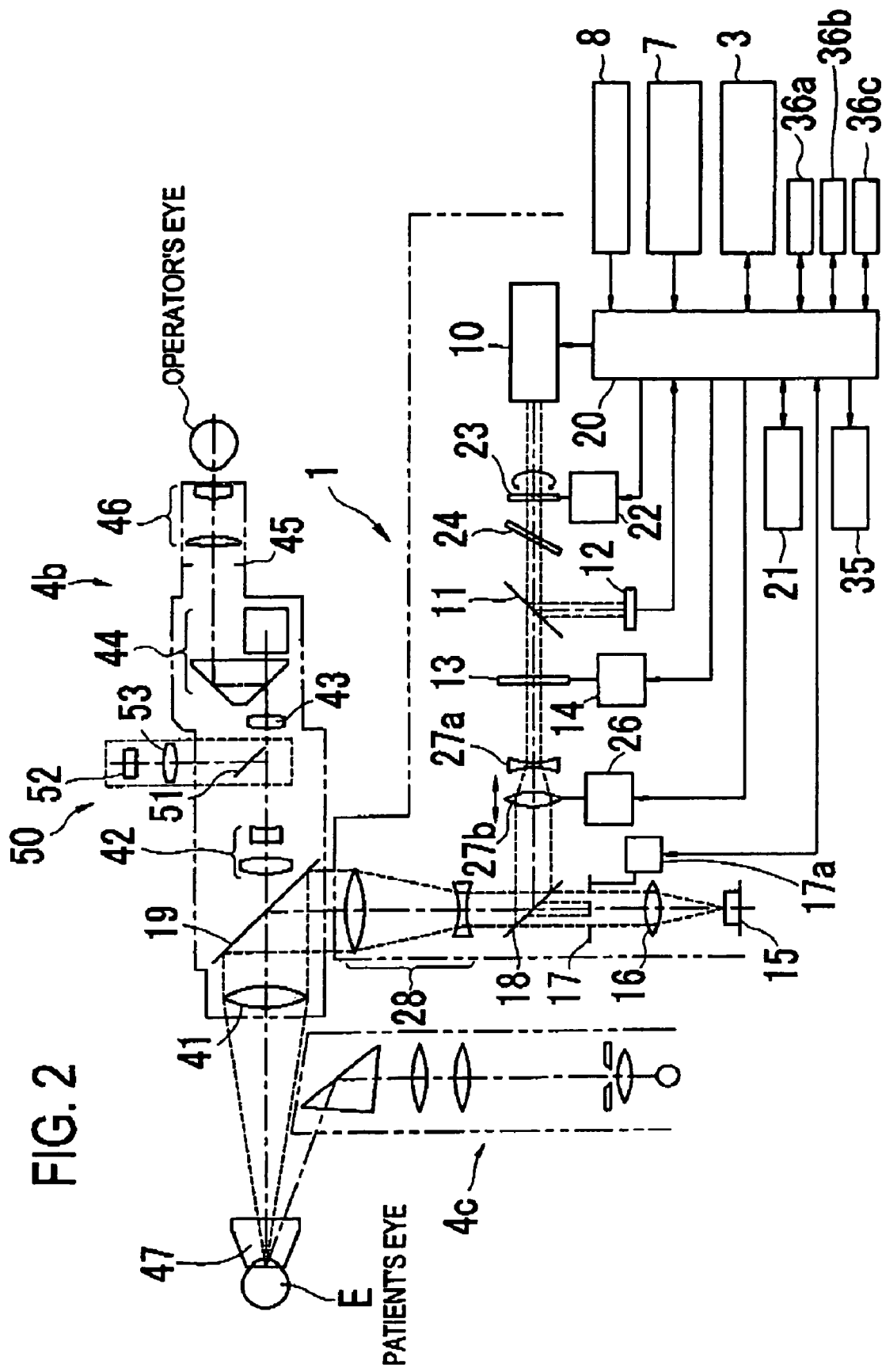
FIG. 2 is a schematic configuration diagram of main parts of an optical system and a control system of the apparatus.

A detailed description of a preferred embodiment of the present invention will now be given referring to the accompanying drawings, exemplifying an ophthalmic laser treatment apparatus adapted for aftercataract treatment, glaucoma treatment, and other treatments, with a treatment laser beam of giant pulses. FIG. 1 is a schematic perspective view of the ophthalmic laser treatment apparatus in the present embodiment. FIG. 2 is a schematic configuration view of main parts of an optical system and a control system of the apparatus.

In a main unit 1 of the apparatus, a laser source 10 for the treatment laser beam, a laser source 15 for an aiming laser beam, an irradiation optical system for irradiating each beam, and others are placed. The main unit 1 is further provided with a switch section for setting irradiation conditions of the treatment beam and the aiming beam. The switch section of the apparatus in the present embodiment includes an adjustment knob 36a for adjusting energy of the treatment beam, an adjustment knob 36b for adjusting a focus shift of the treatment beam, and a rotating knob 36c for rotating the aiming beam, which are arranged on the side surface of the main unit 1, and a control panel 3 having a plurality of switches and displays which are arranged on the operator's side of the main unit 1.

A slit lamp 4 having eyepiece parts 4a comprises a microscope part 4b housing an observation optical system and an illumination part 4c housing an illumination optical system. The main unit 1 and the illumination part 4c are swingably (rotatably) mounted on a slide base 9 which is slidable on a table 2. The microscope part 4b is fixedly placed on the main unit 1. Provided on the patient's side of the slide base 9 is a head rest 6 for fixedly supporting the face (head) of the patient. On the operator's side of the slide base 9, a joystick 5 having a grip 5a which the operator will grasp by his/her hand is located. The slide base 9 is movable with respect to the table 2 by tilting operation of the joystick 5. Specifically, the joystick 5 is supported on a shaft 5b and is tilted backward/forward and rightward/leftward to move the slide base 9 with respect to the table 2 backward/forward and rightward/leftward. When the grip 5a is rotated about the center axis of the shaft 5b, the main unit 1 (together with the microscope part 4b and the illumination part 4c) is moved up and down with respect to the slide base 9. These movements allow alignment (positioning) of the main unit 1 (with the microscope part 4b and the illumination part 4c) with respect to the patient's eye. For the structure of a sliding mechanism and a vertical-movement mechanism by the joystick 5, a well known structure is available. Thus, the detailed explanation thereof is omitted herein.

A head 5c is fixed on the joystick 5. The joystick 5 is provided at the top (the head 5c) with a trigger switch 8 for inputting a trigger signal for irradiation of the treatment beam. In addition, the joystick 5 is provided with a shuttle push switch 7 serving as an auxiliary switch independently from the knobs 36a to 36c and each switch on the control panel 3. The switch 7 is located on the periphery of the joystick 5 slightly above the grip 5a and on the patient's side (the main unit 1 side) so that the operator readily manipulates the switch 7 with his/her forefinger or middle finger while gripping the joystick 5 (the grip 5a).

Figure 3:
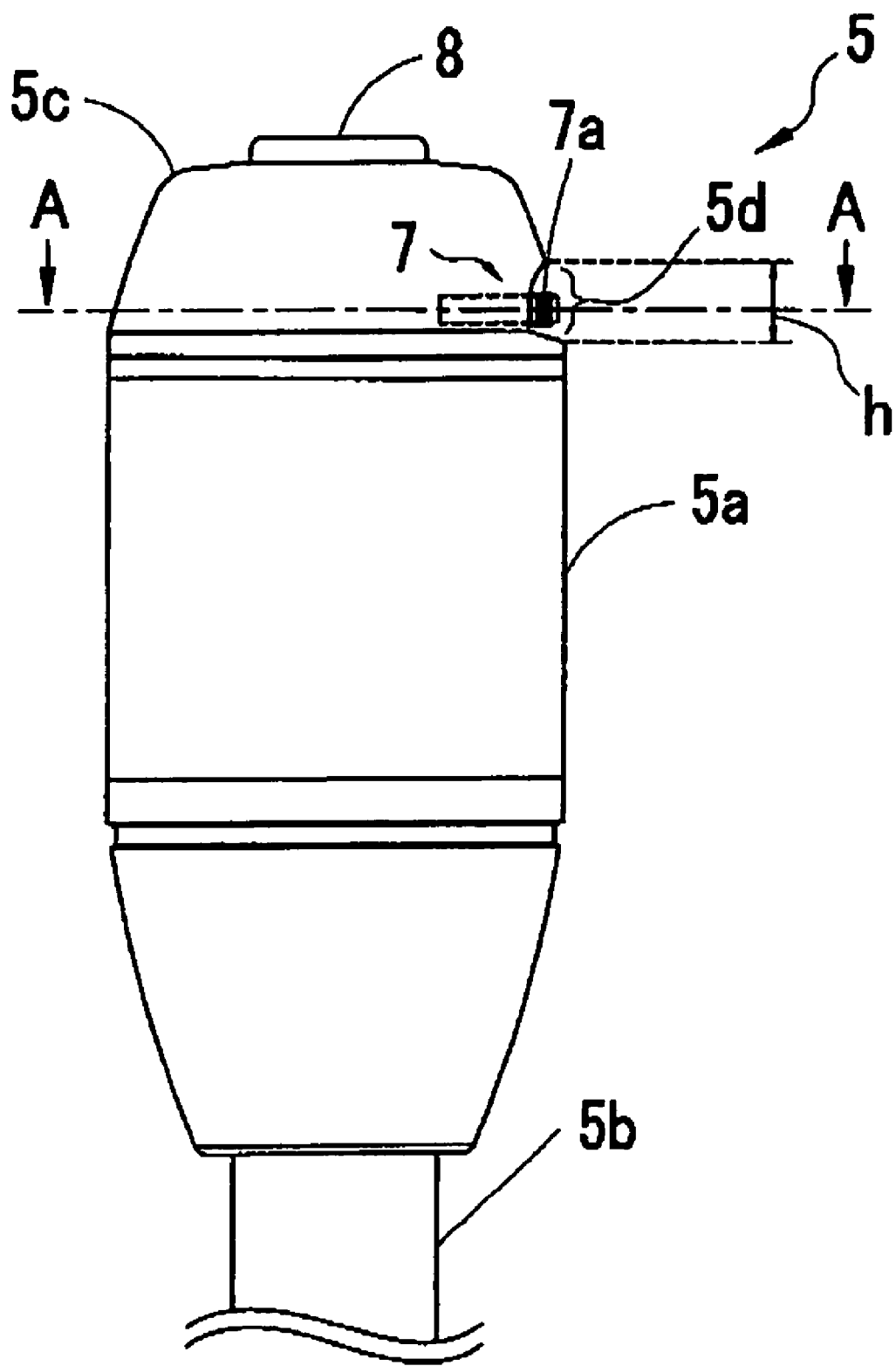
FIG. 3 is a schematic side view of a joystick.
Figure 4A:
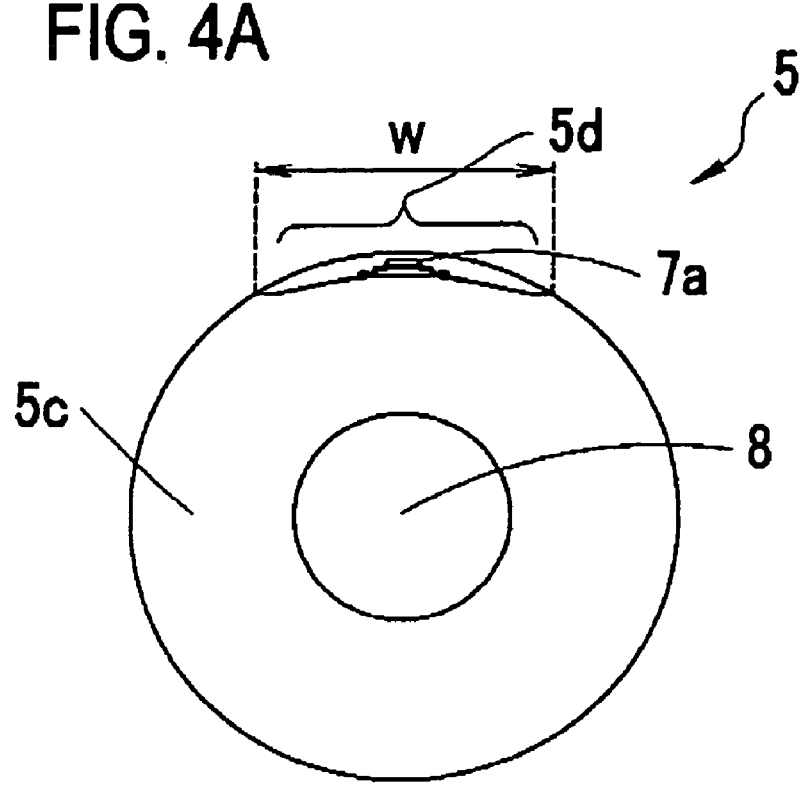
FIG. 4A is a schematic top view of the joystick.
Figure 4B:
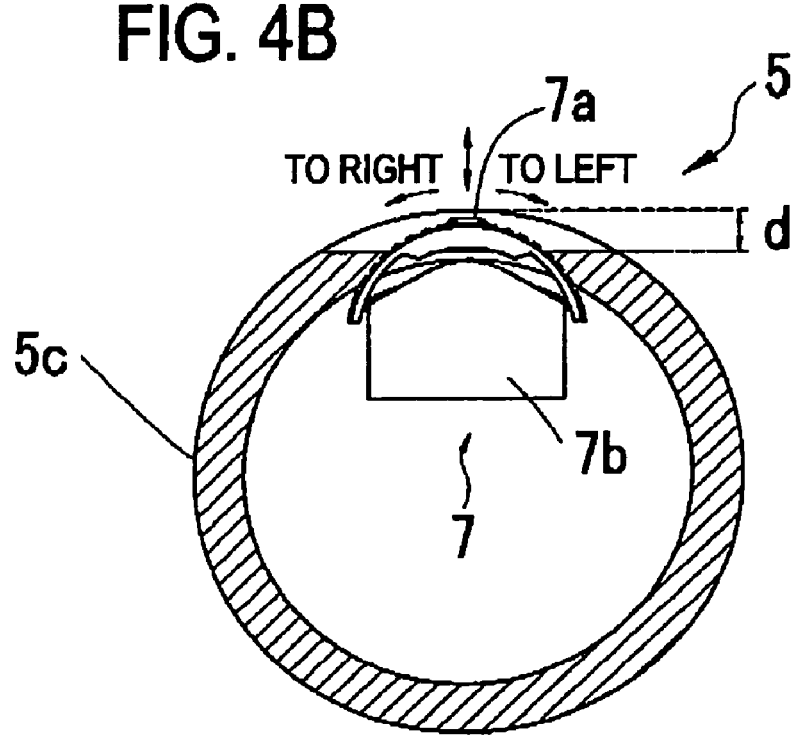
FIG. 4B is a schematic sectional view of the joystick take along a line A-A of FIG. 3, showing a shuttle push switch.

FIG. 3 is a schematic side view of the joystick 5. The right side in the figure corresponds to the patient's side. FIG. 4A is a schematic top view of the joystick 5 and FIG. 4B is a sectional view of the joystick 5 horizontally taken along the portion including the switch 7 and viewed from above (a sectional view taken along a line A-A of FIG. 3).

The switch 7 used in the present embodiment is a switch capable of inputting three switch signals. The switch 7 includes a substrate 7b attached with an arcuate tip 7a. When the tip 7a in a reference position (a state shown in FIGS. 4A and 4B) is pushed toward the center axis of the joystick 5, a first switch signal is input. When the tip 7a is tilted (rotated) rightward (clockwise) from the reference position, a second switch signal is input. When the tip 7a is tilted (rotated) leftward (counterclockwise), a third switch signal is input. In other words, any one of the switch signals remains input while the tip 7a is in a tilted state. When released from the tilted state, the tip 7a is returned to the reference position by a spring built in the substrate 7b, at which any switch signal will not be input.

The switch 7 is located within an opening 5d so that the top of the tip 7a does not protrude from the outer periphery of the joystick 5 (the grip 5a and/or the head 5c). The opening 5d is provided in the outer periphery of the head 5c on the patient's side and as a recess formed in part of the outer periphery (of a maximum diameter) of the head 5c. The opening 5d is designed in a size enough to allow the cushion of a finger (opposite to the nail) of an adult to reach the tip 7a so as to push and tilt (rotate) the tip 7a.

In the present embodiment, the height h of the opening 5d in a vertical direction is about 6 mm, the width w of the same in a horizontal direction is about 18 mm, both of the maximum outside diameter of the head 5c and the outside diameter of the grip 5a are about 33 mm, and the depth d of the opening 5d is about 2.4 mm.

The above arrangement of the switch 7 enables the operator to input the thee switch signals while gripping the joystick 5 (the grip 5a). Since the tip 7a is arranged to hardly protrude from the outer periphery of the joystick 5. This makes it possible to reduce a possibility that the switch 7 may be erroneously operated during tilting or rotating operation of the joystick 5.

It is preferable that the switch 7 is arranged so that the top thereof does not protrude from the outer periphery of the joystick 5, but it should not be limited thereto. The top of the tip 7a may be protrude from the outer periphery of the joystick 5 to the degree that erroneous operations can substantially be prevented. Further, an adjustment mechanism may be added to adjust the protruding length of the top of the tip 7a.

In the above explanation, the switch 7 is disposed in the upper periphery of the joystick 5 on the patient's side. As an alternative, the switch 7 may be disposed in the upper periphery of the joystick 5 on the operator's side to make it easy for the operator to manipulate the switch 7 with his/her thumb while gripping the joystick 5 (the grip 5a). As another alternative, the switch 7 may be disposed in the lower periphery of the joystick 5 on the patient's side to make it easy for the operator to manipulate the switch 7 with his/her annular finger or little finger while holding the joystick 5 (the grip 5a). The switch 7 may also be provided in a position shifted to the right or left from that in FIGS. 4A and 4B. Furthermore, the switch 7 may be provided in the middle periphery of joystick 5 (the grip 5a) if the grip 5a is configured not to rotate.

The switch 7 is arranged to tilt (rotate) in a right and left (horizontal) direction in the above explanation. Alternatively, the switch 7a may be arranged to tilt (rotate) in an upward and downward (vertical) direction. In this case, the opening 5d is formed in a longer shape in the vertical direction.

The switch 7 is not limited to the shuttle push switch and may be any switch capable of inputting a switch signal by pushing of the tip 7a and a switch signal by tilting (rotating) of the tip 7a.

The laser source 10 comprises a solid-state laser rod such as an Nd:YAG rod, an excitation light source, a Q-switch, and others and is adapted to emit the treatment beam of giant pulses having a narrow pulse width and a large peak energy. The infrared treatment beam emitted from the laser source 10 falls on a dichroic mirror 18 which reflects an infrared beam while transmitting a visible beam, via a ½ wave plate 23, a polarization plate 24 disposed at a Brewster angle, a half mirror 11 which reflects part of an infrared beam while transmitting major part thereof, a concave lens 27a, and a convex lens 27b. The ½ wave plate 23 is rotated by a rotation part 22 such as a motor to be driven under control of a controller 20. By combination of the ½ wave plate 23 and the polarization plate 24, the energy of the treatment beam to be irradiated is adjusted. A photodetector 12 detects the treatment beam reflected by the half mirror 11 to obtain (measure) the energy. A safety shutter 13 is placed to be moved into or out of the optical path of the treatment beam by a movement part 14 such as a solenoid to be driven under control of the controller 20.

The aiming beam emitted from the laser source 15 such as a semiconductor laser source is formed into a collimated beam by a collimator lens 16, split in two beams by an apertured plate 17 having two apertures, and falls on the dichroic mirror 18. The apertured plate 17 is rotated about the optical axis of the collimator lens 16 by a rotation part 17a such as a motor to be driven under control of the controller 20, thereby rotating the orientation of the two split aiming beams arranged side by side is rotated.

The treatment beam and the aiming beam made coaxial with each other by the dichroic mirror 18 pass through an expander lens 28 and are reflected by a dichroic mirror 19 which reflects an infrared beam and part of a visible beam while transmitting major part of the visible beam in the microscope part 4b. The reflected beams are then focused on an affected part of a patient's eye E via an objective lens 41 and a contact lens 47.

A focal point of the treatment beam can be shifted in a depth direction of the eye E (in a direction of the optical axis of the objective lens 41) with respect to a focal point of the aiming beam. This shift is made by the controller 20 that drivingly controls a movement part 26 such as a motor based on a set amount and a ret direction of the focus shift which will be mentioned later to move a convex lens 27 in the optical axis direction.

The observation optical system in the microscope part 4b includes the objective lens 41 and the dichroic mirror 19, which are used in common for the right and left observation optical paths, a variable power optical system 42, an image forming lens 43, erect prisms 44, a field diaphragm 45, and eyepiece lenses 46, which are placed in each of the right and left optical paths.

In the observation optical system in the microscope part 4b, an in-field display system 50 is incorporated so that set values of the irradiation conditions of the treatment beam and the aiming beam appear within the visual field. The in-field display system 50 is provided with a double-faced mirror 51 placed at a slant between the variable power optical system 42 and the image forming lens 43 in one of the observation optical path. Above the double-faced mirror 51, a display part 52 consisting of a light emitting element such as an LED and a collimator lens 53. The display part 52 is placed in conjunction with a field diaphragm 45.

Figure 5:
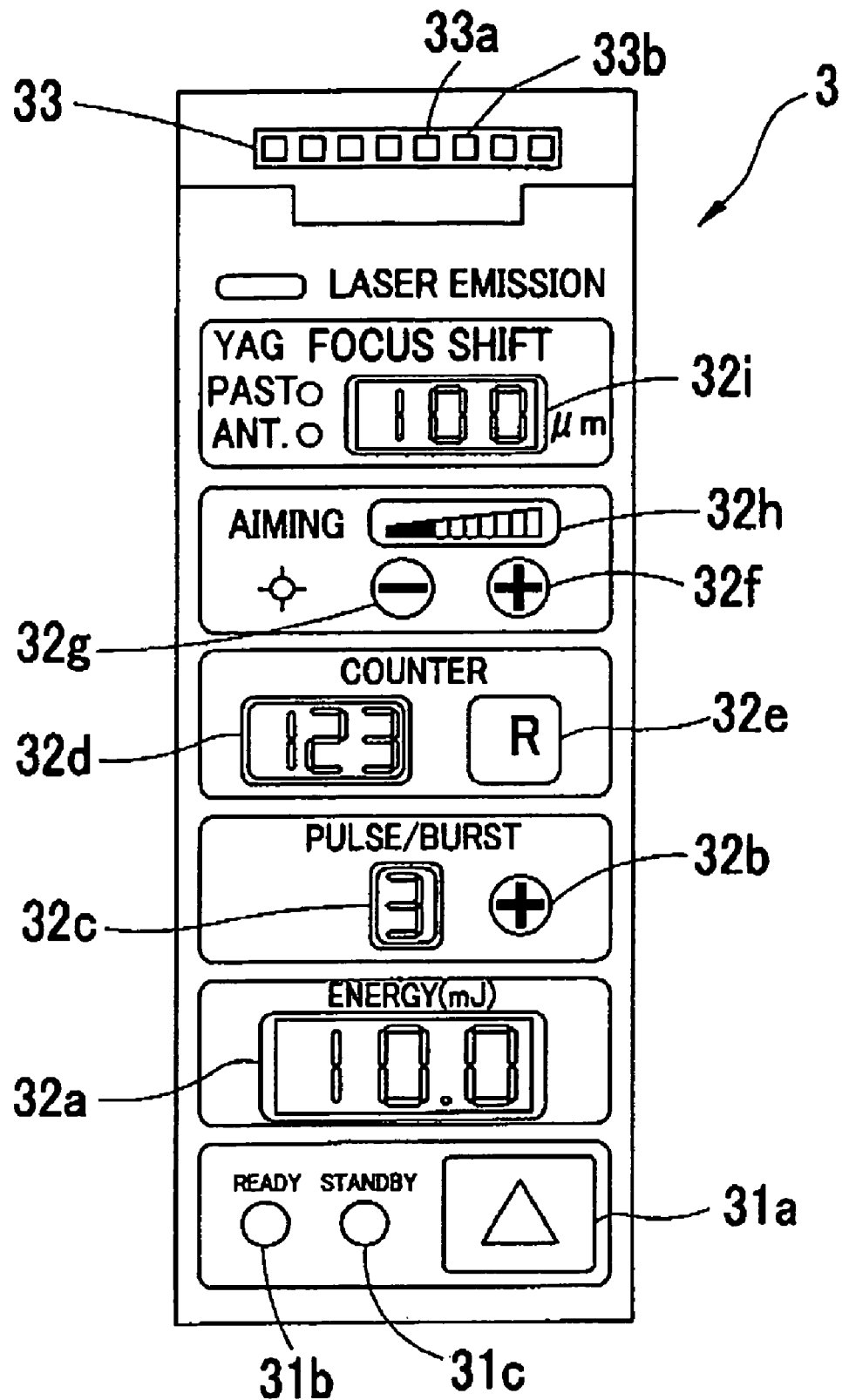
FIG. 5 is a schematic front view of a control panel.

FIG. 5 is a schematic front view of the control panel 3. A switch 31a is used to switch between a READY mode where the treatment beam will be irradiated upon input of the trigger signal and a STANDBY mode where the treatment beam will not be irradiated even upon input of the trigger signal. An indicator 31b lights up in the READY mode. An indicator 31c lights up in the STANDBY mode.

A display 32a displays a set value of the energy of the treatment beam. A switch 32b is used to set the number of irradiation pulses of the treatment beam for one trigger signal. This set value is displayed in a display 32c. A display 32d displays a set value for the number of irradiations of the treatment beam, which is reset with a switch 32e. Switches 32f and 32g are used to increase/decrease the light quantity of the aiming beam, the light level of which is displayed in a display 32h. A display 32i displays a set value of a focus shift amount of the treatment beam. A setting part 33 is used to change allocation of functions to the switch signals of the switch 7. When not in use, the setting part 33 is covered with a cover.

Operations of the laser treatment apparatus having the above structure will be explained below. Herein, the first switch signal to be generated at the push of the tip 7a of the switch 7 is allocated a function of switching the operation modes of the apparatus. For example, it is assumed that the first switch signal is allocated the same function as the switch 31a (switching between the READY mode and the STANDBY mode). The second switch signal to be generated when the tip 7a is tilted to the right and the third switch signal to be generated when the tip 7a is tilted to the left are allocated symmetrical functions such as adjustment (increase/decrease) functions for the set values of the treatment beam and/or the aiming beam. For example, it is assumed that those signals are allocated the same function as the knob 36a (adjustment of the energy of the treatment beam). The function allocation data on the switch signals are stored in a memory 21.

In the allocation of functions to the switch signals, preferably, the switching function of the operation modes of the apparatus is allocated to the first switch signal and the symmetrical functions such as adjustment (increase/decrease) functions of the set values of the treatment beam and/or the aiming beam are allocated to the second and third switch signals. The allocations are not limited to above. The switching function of the operation modes of the apparatus may be allocated to the second and third switch signals. Further, the above three switch signals are allocated each function, but it is not limited thereto. For example, the first switch signal may be disabled.

Prior to treatment, the switches on the control panel 3 and the knobs 36a to 36c are operated to set irradiation conditions of the treatment beam and the aiming beam, and others. The energy of the treatment beam may be set with the switch 7. The eye E illuminated by illumination light from the illumination part 4c is observed through the microscope part 4b. The main unit 1 is moved by operation of the joystick 5 and the knob 5a so that the aiming beam is aligned to the affected part. This alignment using the aiming beam is performed so that two separate spots of the aiming beams are concentrated as a single spot on the affected part. The operator holds the contact lens 47 with his/her one hand while grasping the joystick 5 with the other hand. After completion of the alignment, the mode is to be switched from the STANDBY mode to the READY mode. In this case, the switching can be made by operation of the switch 7 provided in the joystick 5 even if the operator does not take the trouble to take his/her hand off the joystick 5 and operate the switch 31a.

When switched to the READY mode, the controller 20 causes the shutter 13 to move out of the optical path of the treatment beam. Upon receipt of the trigger signal from the switch 8 when pressed, the controller 20 causes the laser source 10 to emit the treatment beam. The treatment beam is irradiated to the affected part of the eye E by the aforementioned irradiation optical system. The affected part irradiated with the treatment beam is observed. When a treatment effect is too low or too high, the energy of the treatment beam is adjusted. This adjustment can also be performed by operation of the switch 7 provided in the joystick 5 even if the operator does not take the trouble to take his/her hand off the joystick 5 and operate the knob 36a.

Figures 6, 7:
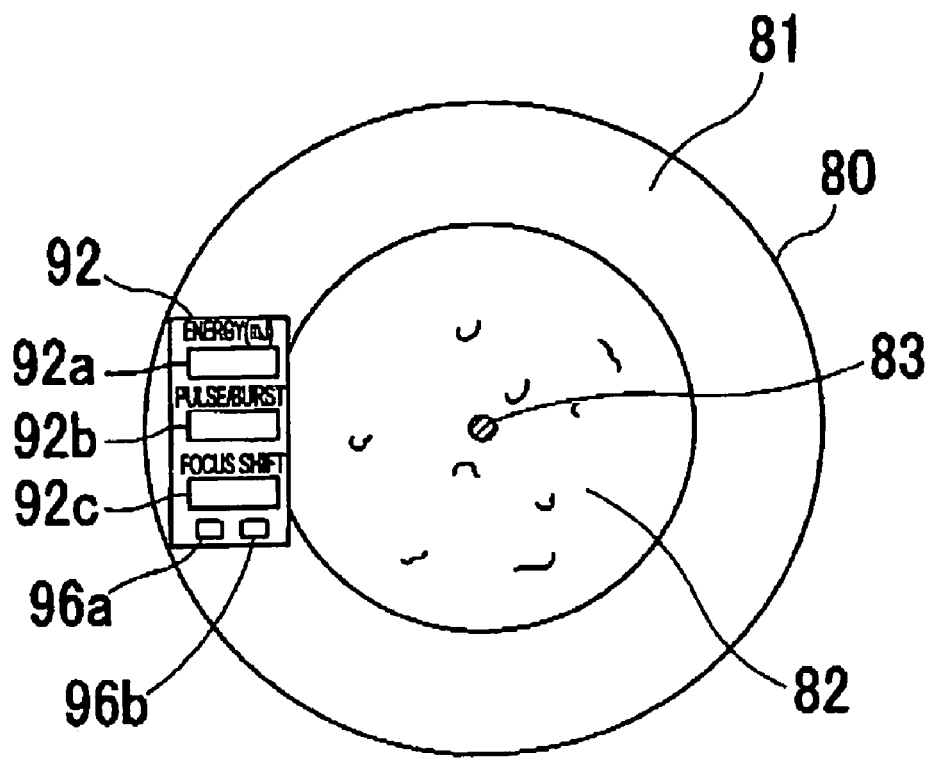
FIG. 6 is a view showing an observation visual field with a display function.
FIG. 7 is a table showing combination patterns of functions of three switch signals.

The set value of the energy of the treatment beam can be chocked in the display 32a. It is more preferable for the operator to make sure it without taking his/her eyes from the eyepiece parts 4a. For this end, a display 92 representing irradiation conditions is given in an observation visual field 80 as shown in FIG. 6. In FIG. 6, numeral 81 denotes the iris of the eye E under observation; 82, the posterior capsule of crystalline lens clouded; and, 83, the aiming beam. The display 92 includes a display 92a of the energy of the treatment beam, a display 92b of the number of irradiation pulses of the treatment beam, a display 92c of the focus shift amount of the treatment beam, a display 96a indicating the READY mode, and a display 96b indicating the STANDBY mode.

The irradiation conditions changed with the switch 7 may be announced by voice through a speaker 35.

The functions of the switch signals of the switch 7 may be changed by the setting part 33 according to operator's preferences. Upon press of a switch 33a of the setting part 33, a mode of changing the functions of the switch signals is established. In this mode, the switches and displays on the control panel 3 are also used as the switches and displays for the changing. For example, in the case that the function of the first switch signal to be generated at the push of the tip 7a is to be changed from the same function as that allocated to the switch signal of the switch 31a to the same function as that allocated to the switch signal of the switch 32b, in the case that the second and third switch signals by tilting of the tip 7a in the right and left directions are to be changed from the same function as that allocated to the switch signal of the knob 36a to the same function allocated to the switch signals the switches 32f and 32g, or in other cases, the switch 33a is pressed to establish the function changing mode in which the function allocation is changed with the switches and the displays on the control panel 3. The function changing mode is released when the switch 33a is pressed again, updating data on the function allocation to the switch signals of the switch 7 stored in the memory 21.

As above, the functions allocated to the switch signals of the switch 7 provided in the joystick 5 can be changed and therefore the switches in small number can be utilized effectively. When the function allocation to the switch signals of the switch 7 is changed, the display 92 in the observation visual field 80 is changed accordingly.

It is to be noted that the functions of the first, second, and third switch signals of the switch 7 may be changed to previously recorded ones. For example, the function of the first switch signal may be changed in turn between the function of switching between the READY and STANDBY modes and the function of switching to a burst mode every time the tip 7a is pushed for a longer period (e.g., two seconds or more). The functions of the second and third switch signals may be changed in turn between the function of adjusting (increase/decrease) of the energy of the treatment beam and the function of adjusting (increase/decrease) of the light quantity of the aiming beam every time the tip 7a is tilted to the right or left for a longer period. A mechanism for changing the functions of the first to third switch signals of the switch 7 may be provided in the joystick 5 itself. The function change can be further facilitated.

The functions of the first, second, and third switch signals of the switch 7 may be changed in such a manner that a plurality of combination patterns of functions of three switch signals is recorded in advance and a desired combination pattern is selected therefrom. FIG. 7 is a table showing the combination patterns of the functions of the three switch signals. Pattern 1 is a combination of the above mentioned initial settings that the first switch signal is allocated the function of switching between the READY and STANDBY modes, the second switch signal is allocated the function of increasing the energy of the treatment beam, and the third switch signal is allocated the function of decreasing the energy of the treatment beam. Pattern 2 is a combination that the first switch signal is allocated the function of switching to the burst mode (the same function as that of the switch 32b), the second switch signal is allocated the function of increasing the light quantity of the aiming beam (the same function as that of the switch 32f), and the third switch signal is allocated the function of decreasing the light quantity of the aiming beam (the same function as that of the switch 32g). Pattern 3 is a combination that the first switch signal is allocated the function of rotating the aiming beam (the same function as that of tho knob 36c), the second switch signal is allocated the function of increasing the focus shift of the treatment beam in a backward direction (the same function as that of the knob 36b), and the third switch signal is allocated the function of increasing the focus shift of the treatment beam in a forward direction (the same function as that of the knob 36b).

The above pattern combinations are recorded in a combination pattern recording mode which is established upon press of the switch 33b of the Betting part 33. In this mode, the switches and displays on the control part 3 are also used as the switches and displays for the recording operation. After record of the combination patterns, the switch 33b is pressed again to release the combination pattern recording mode, updating the data on recoded combination patterns of the functions of the switch 7 in the memory 21.

Consequently, in the case where a single apparatus is used in common among plural operators, a combination pattern of the function of each switch signal of the switch 7 can be changed according to individual operator's preferences.

The present invention may also be applied to an ophthalmic laser treatment apparatus for photocoagulation treatment and others. To be concrete, an apparatus having an illumination and observation optical system and an irradiation optical system for a treatment laser beam includes a joystick for alignment (positioning) of those optical systems to a patient's eye. Accordingly, the joystick 5 is provided with the switch 7 as in the above example. In the apparatus for photocoagulation treatment, for example, each switch signal of the switch 7 may be allocated each of the function of adjusting the spot size of the treatment beam, the function of adjusting a coagulation time (an irradiation time of the treatment beam), the function of adjusting a halt time, switching between a single mode and a repeat mode (a mode in which a coagulation time and a halt time are alternately repeated while a trigger signal is being input), and other functions.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. An ophthalmic laser treatment apparatus comprising:
   a main unit in which an illumination and observation optical system for illuminating a patient's eye and allowing observation of the patient's eye under illumination, and an irradiation optical system for irradiating a treatment laser beam and an aiming beam to the patient's eye;
   a joystick including a grip to be grasped by an operator, the joystick being configured to move the main unit with respect to the patient's eye;
   a first switch provided at a top of the joystick and used to input a trigger signal for irradiation of the treatment beam;
   a second switch placed in an opening formed in one of an upper side and a lower side of the joystick relative to the grip so that the second switch can be operated with fingers of the operator who grasps the grip and a top of the second switch does not protrude from an outer periphery of the joystick, the second switch being a switch for inputting a plurality of switch signals, configured to input a first switch signal when pushed toward a center axis of the joystick and input a second switch signal and a third switch signal when tilted or rotated in one of a rightward and leftward direction and an upward and downward direction; and
   changing means for changing functions of the switch signals to be inputted by the second switch.

2. The ophthalmic laser treatment apparatus according to claim 1, wherein the first switch signal is a signal for switching an operation mode of the apparatus.

3. The ophthalmic laser treatment apparatus according to claim 1, wherein the second and third switch signals are signals for increasing and decreasing a set value of one of the treatment beam and the aiming beam.

4. The ophthalmic laser treatment apparatus according to claim 3, wherein the second and third switch signals are signals for increasing and decreasing a set value of one of energy of the treatment beam and a focus shift amount of the treatment beam.

5. The ophthalmic laser treatment apparatus according to claim 1 further comprising:
   storage means for storing a plurality of combination patterns of the functions of the first, second, and third switch signals,
   wherein the changing means selects one from the plurality of patterns stored in the storage means to change the functions of the switch signals set to the second switch.

6. The ophthalmic laser treatment apparatus according to claim 1 further comprising:
   storage means for storing a plurality of functions corresponding to each switch signal,
   wherein the changing means selects one from a plurality of patterns stored in the storage means to change the functions of the switch signals set to the second switch.

7. The ophthalmic laser treatment apparatus according to claim 6, wherein the changing means includes the second switch, any one of input of the switch signal and change of the function is performed by difference of operation time of the switch.

* * * * *